US006025168A

United States Patent [19]
Vercauteren et al.

[11] Patent Number: 6,025,168
[45] Date of Patent: Feb. 15, 2000

[54] METHOD FOR THE PRODUCTION OF ISOMALTO-OLIGOSACCHARIDE RICH SYRUPS

[75] Inventors: Ronny Leontina Marcel Vercauteren, Beveren; Van Sau Nguyen; Harald Wilhelm Walter Róper, both of Brussels, all of Belgium

[73] Assignee: Cerestar Holding B.V., Netherlands

[21] Appl. No.: 09/070,655

[22] Filed: May 1, 1998

[30] Foreign Application Priority Data

May 2, 1997 [GB] United Kingdom .................. 9708893

[51] Int. Cl.[7] ........................... C12P 19/18; C12P 19/16; C12P 19/04; C12N 9/10; C12N 11/02

[52] U.S. Cl. ................................ 435/97; 435/94; 435/98; 435/101; 435/177; 435/180; 435/193; 435/200; 435/204; 435/210

[58] Field of Search ............................... 435/94, 101, 97, 435/193, 177, 180, 210, 200, 204, 98

[56] References Cited

U.S. PATENT DOCUMENTS

| | | | |
|---|---|---|---|
| 3,935,070 | 1/1976 | Suekane et al. | 435/94 |
| 4,898,820 | 2/1990 | Hitoshio et al. | 435/95 |

OTHER PUBLICATIONS

Database WPI, Section Ch, Week 9214, Derwent Publications Ltd., London,GB;Class D13, AN 92–110004 XP002048724 & JP 04 051 899 Feb. 20, 1992.

Database WPI Section Ch, Week 8825 Derwent Publications Ltd., London GB; Class B04, AN 88–171782 XP002048725 & JP 63 109 790 A, May 1988.

Database WPI, Section Ch, Week 8803, Derwent Publications Ltd., London, GB; Class D16, AN 88–017460 XP002048726 & JP 62 278 984 A, Dec. 1987.

Database WPI, Section Ch, Week 9139, Derwent Publications Ltd., London GB; Class D13, AN 91–284370 XP002048719 & JP 03 187 390 A Aug. 15, 1991.

Database WPI Section Ch, Week 8644 Derwent Publications Ltd., London, GB; Class B03, AN 86–288889 XP002048720 & JP 61 212 296 A, Sep. 1986.

*Primary Examiner*—Herbert J. Lilling
*Attorney, Agent, or Firm*—Pillsbury Madison & Sutro LLP

[57] ABSTRACT

The present invention describes a method for the production of isomalto-oligosaccharides syrups. The method comprises the use of enzymes immobilized on a re-usable carrier. The carrier is preferably an anion exchanger. The enzymes used for the conversion of starch hydrolysates are transglucosidase and pullulanase preferably these enzymes are co-immobilized. The carrier/enzyme conjugate is further reinforced by cross-linking.

19 Claims, 1 Drawing Sheet

METHOD FOR THE PRODUCTION OF ISOMALTO-OLIGOSACCHARIDE RICH SYRUPS

TECHNICAL FIELD

The present invention describes a method for the production of isomalto-oligosaccharides syrups. The method comprises the use of enzymes immobilized on a re-usable carrier. The invention further relates to syrups obtained by the use of said immobilised enzymes on re-usable carriers and to the use of the said syrups.

BACKGROUND OF THE INVENTION

Isomalto-oligosaccharides syrups contain a substantial amount of branched oligo-saccharides such as isomaltose, pannose, isomaltotriose, isomaltotetraose, nigerose, kojibiose, isopanose and higher branched oligo-saccharides. The products are sold in powder or liquid form, depending on the intended application. The potential applications are situated in the food area examples are:

- seasonings (mayonnaise, vinegar, soup base etc.)
- confectionery (candy, chewing gum, chocolate, ice cream, sherbet, syrup, pate)
- processed foods of fruits and vegetables (jam, marmalade, fruit sauces, pickles), meat or fish foods (ham, sausage, etc.)
- bakery products (bread, cake, cookie)
- precooked foods (salad, boiled beans, etc.)
- canned and bottled foods, drinks (coffee, juice, nectar, aerated drinks, lemonade, cola)
- convenience foods (instant coffee, instant cake base, etc.).

Isomalto-oligosaccharide syrups can further be applied as ingredients in animal feed and pet foods. Non-food application areas are cosmetics and medicine (cigarette, lipstick, toothpaste, internal medicine, etc.).

It is known for some years that isomalto-oligosaccharides are related to the increase of the general well being of humans and animals when taken orally on a regular daily basis. The main action of the oligosaccharides is to increase the numbers of bifidobacteria and lactobacilli in the large intestine and to reduce the concentration of putrifactive bacteria. Bifidobacteria are associated with some health promoting properties like the inhibition of the growth of pathogens, either by acid formation or by anti-microbial activity. They are also associated with such divers effects as the modulation of the immune system (anti-tumor properties), the reduction of the levels of triglycerides and cholesterol, the production of vitamins (B group), the reduction of blood ammonia concentrations, the prevention of translocation, the restoration of the normal gut flora after anti-microbial therapy, the production of digestive enzymes, the reduction of antibiotic associated side effects (Kohmoto T., Fukui F., Takaku H., Machida Y., et al., Bifidobacteria Microflora, 7(2)(1988),61–69; Kohmoto K., Tsuji K., Kaneko T. Shiota M., et al., Biosc. Biotech. Biochem., 56(6)(1992),937–940; Kaneko T, Kohmoto T., Kikuchi H., Fukui F., et al., Nippon Nõgeikagaku Kaishi, 66(8)(1992), 1211–1220, Park J-H, Jin-Young Y., Ok-Ho S., Hyun-Kyung S., et al., Kor. J. Appl. Microbiol. Biotechnol., 20(3)(1992), 237–242).

The isomalto-oligosaccharides are synthesized by a transglucosylation reaction using a D-glucosyltransferase (E.C. 2.4.1.24, transglucosidase, alpha-glucosidase). This enzyme catalyzes both hydrolytic and transfer reactions on incubation with alpha-D-gluco-oligosaccharides. The transfer occurs most frequently to 6-OH (hydroxyl group 6 of the glucose molecule), producing isomaltose from D-glucose, or panose from maltose. The enzyme can also transfer to the 2-OH or 3-OH of D-glucose to form kojibiose or nigerose, or back to 4-OH to reform maltose. As a result of transglucosidase reactions, the malto-oligosaccharides are converted into isomalto-oligosaccharides resulting in a class of oligosaccharides containing a higher proportion of glucose moieties linked by alpha-D-1,6 glucosidic linkages. The transglucosidase from A.niger acts only on oligosaccharides with a low DP (McCleary B. V., Gibson T. S., Carbohydrate Research 185(1989)147–162; Benson C. P., Kelly C.T., Fogarty W. M., J. Chem. Tech. Biotechnol., 32(1982) 790–798; Pazur J. H., Tominaga Y., DeBrosse C. W., Jackman L. M., Carbohydrate Research, 61(1978) 279–290).

Isomalto-oligosaccharides can be obtained in different ways. For example glucose syrups at high dry solids concentration i.e. 60–80% are treated with glucoamylase resulting in the formation of isomalto-oligosaccharides mainly DP2. Other examples are maltose transfer achieved by addition of pullulanase to liquefied starch, branching of maltose syrups and treatment of sucrose with dextran sucrase.

Commercial production of isomalto-oligosaccharides is reported to be performed in a non-continuous manner. A normal production method (JP 61-212296, Showa Sangyo Co. Ltd.) starts with the liquefaction of a 30% ds slurry of corn, potato or tapioca starch with a thermostable alpha-amylase to a 6 to 10 DE liquefact. This liquefact is brought to pH 5 and 60° C., and beta-amylase and transglucosidase are added and the saccharification is continued for 48–72 h. At the end of the saccharification period, the syrup is filtered and refined with active carbon and ion-exchangers. The pure product is finally concentrated to around 80% ds (Takaku H., Handbook of Amylases and related enzymes, Ed. The Amylase Research Society of Japan, Pergamon Press, Oxford, (1988), 215–217). The beta-amylase used originates from soy-bean or wheat, the transglucosidase mostly comes from a fungal source, preferably *Aspergillus niger.*

Other production methods are known, these include the conversion of starch hydrolysate with a mixture of alpha-amylase and transglucosidase (JP 41-48693, Nippon Corn Starch KK) and the conversion of starch into a high DP3 or DP4 syrup with DP3 or DP4 forming alpha-amylases in conjunction with transglucosidase to produce branched oligosaccharides (JP 31-87390, Gunei, Kagaku Kogyo).

A lot of attention has been paid to soluble enzyme systems for the production of isomalto-oligosaccharides, no such activity can be seen in the field of immobilised enzymes. Japanese patent application JP63-109790 (assigned to Showa Sangyo Co.) describes the use of an immobilised transglucosidase conjugate for the production of isomalto-oligosaccharide syrups. The conjugate is made by cross-linking of gelatin with glutaric dialdehyde in the presence of transglucosidase. The obtained conjugate has a low mechanical stability, and has to be ground before transport to the holding columns is possible. Due to the rather heterogeneous reaction the enzyme is not distributed homogeneously inside the carrier material, which leads to disturbed kinetics, yielding an end product which has not the maximally obtainable amount of isomalto-oligosaccharides. A further disadvantage is that the carrier is not reusable. After exhaustion of the enzyme activity, the whole conjugate has to be thrown away which is economically and ecologically a not preferred solution.

European patent application EP 301522 relates to the production of isomaltulose starting from a mixture of glucose and fructose. The description does not disclose the use of re-usable carriers for this mentioned process in addition the examples show only the use of non-immobilised enzymes for performing the conversion.

U.S. Pat. No. 3,935,070 relates to the isomerisation of a starch hydrolysate to convert at least a part of the dextrose to levulose. This conversion may be followed by a treatment with transglucosidase on bentonite. Bentonite is not a re-usable carrier. Moreover the starting material is a dextrose mother liquor.

Japanese patent application JP04 051899 (assigned to NGK Insulators Ltd.) discloses the use of enzymes immobilised on porous ceramic particles composed of $SiO_2$ and MgO. These ceramic particles are not re-usable.

Japanese patent application JP62 278984 (assigned to Daikin Kogyo KK) disloses the use of a co-immobilisate composed of cells and enzymes. Also such a product is not re-usable.

SUMMARY OF THE INVENTION

The present invention describes a method for producing isomalto-oligosaccharides syrups wherein a starch hydrolysate is enzymatically converted by a transglucosidase using a re-usable carrier for the immobilisation of the transglucosidase. The starch hydrolysate is a syrup having a DE between 4 and 70, preferably between 20 and 60.

Preferably, the carrier is an anion exchange resin and the transglucosidase is immobilized onto it by adsorption.

It is a further aspect of the invention that other enzymes are co-immobilized with the transglucosidase, such other enzymes are a pullulanase or an alpha-amylase. The enzymes maybe immobilised together on the same carrier, but it is also possible to immobilise the enzymes seperately. This makes it possible to separate the two enzymatic conversion steps.

In another aspect of the invention the carrier/enzyme conjugate is further reinforced by reaction with one or more cross-linking agents.

The continuous production of an isomalto-oligosaccharide syrup containing more than 40% isomalto-oligosaccharides is disclosed, preferably more than 45%. These values are achieved with a flow rate of at least 3 bed volumes per hour and for a period of at least 25 days.

In yet another aspect the isomalto-oligosaccharide syrup is refined i.e. further treated by chromatographic means or by filtration.

It is still another part of the invention that during the production of the isomalto-oligosaccharide syrup or thereafter the sweetness is increased. This can be done by addition of a sweetener or by an additional enzymatic conversion with glucose isomerase or a hydrolase whereby glucose is converted to fructose. This enzymatic conversion can be performed simultaneously with or succesively to the transglucosylation.

DETAILED DESCRIPTION OF THE INVENTION

Figure 1:
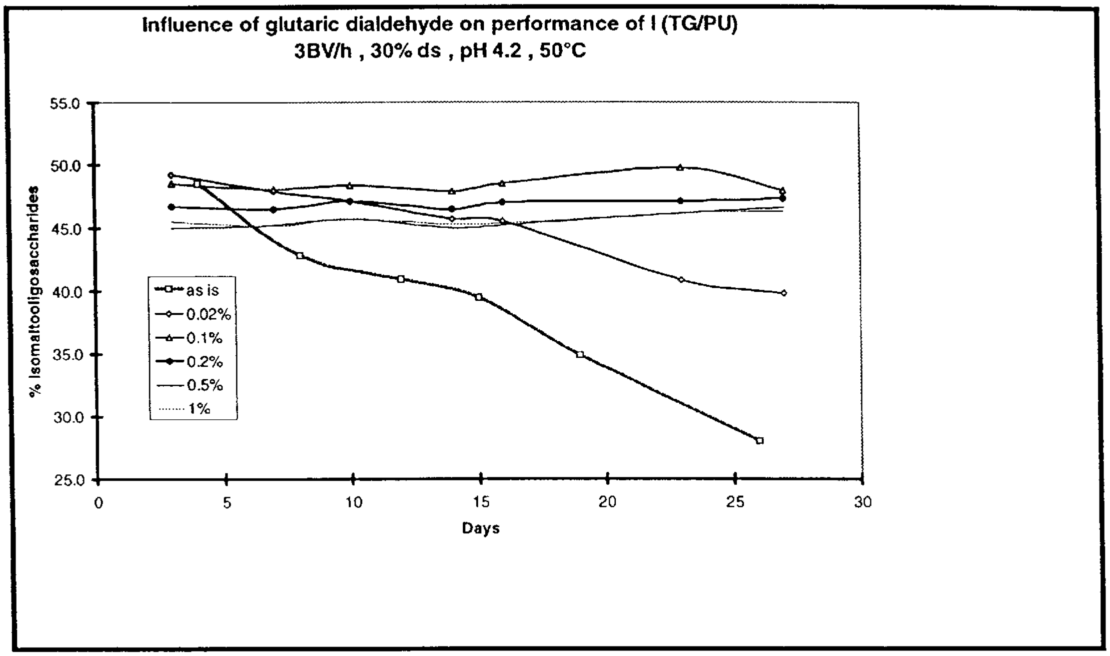
FIG. 1 shows the production of isomalto-oligosaccharides (=% isomaltose+% nigerose+% isomaltotriose+% panose+% isomaltotetraose) as a function of the life time of the conjugate and the amount of glutaric dialdehyde used for cross-linking.

The present invention describes a method for producing isomalto-oligosaccharides syrups wherein a starch hydrolysate is enzymatically converted by a transglucosidase or an enzyme having comparable activity, using a re-usable carrier for enzyme immobilisation. The starch hydrolysate has a DE between 4 and 70, preferably between 20 and 60. The starch hydrolysate is obtained for example, by enzymatic or acid hydrolyses in accordance with known in the art.

As a carrier any re-usable material can be used. For the present purpose re-usable means that the carrier can be freed of enzyme or enzymatic activity in such a way that the carrier material stays intact. The carrier material can then be re-loaded with enzyme and re-used. The cleaning of the carrier can for example be performed by washing with acidic or basic solution this may be done in batch or in the column. It may be advantageous to add a salt. Another possibility is the use of protein degrading enzymes. Yet another means would be heating of the material.

Preferably, materials are used which have anion exchange groups. Such materials may be on the basis of cellulose. Other more preferred carriers are polyacrylate or polystryrene based carriers having weakly basic groups, preferred are phenolformaldehyde based carriers such as Duolite™ A 568 (Rohm and Haas).

Preferably, the carrier is an anion exchange resin and the transglucosidase is immobilized onto it by adsorption i.e in a non-covalent manner. This enables the easy removal of the inactive enzyme and the subsequent reloading with fresh enzyme. It is shown in the presented examples (notably in example 11) that the enzyme can be easily removed from the carrier. Reloading of the carrier resulted in complete recovery of the activity of the conjugate. This means that the carrier material can be used for a considerable period of time before it has to be replaced.

Example 1 illustrates the immobilisation of transglucosidase on an anion exchange resin. Application of this catalyst in a column for the conversion of a 30% ds maltose syrup shows that at a constant flow rate of about 3 bed volumes per hour the total amount of isomalto-oligosaccharides formed is about 40% and the process is stable for at least about 30 days. A small change in the amount of individual isomalto-oligosacchardies is observed. The activity of the enzyme is mainly in the DP2–DP6 range. The cross-linking of the immobilised transglucosidase with glutaric dialdehyde is described in Example 2. The dialdehyde was used at a final concentration of 1%. Results (Example 2) show that the cross-linking of the enzyme gives rise to the formation of a syrup having a different composition from the one obtained without cross-linking. Specifically, the amount of glucose is increased. The total amount of isomalto-oligosaccharides is about 35% the decrease of 5% can almost completely be ascribed to a decrease in panose.

It is a further aspect of the invention that other enzymes are co-immobilized with the transglucosidase, such other enzymes are pullulanases or alpha-amylases. The pullulanase or alpha-amylase will degrade higher DPn fractions into smaller fragments, which are accessible for the action of transglucosidase. The enzymes may be immobilised together on the same carrier, but it is also possible to immobilise the enzymes separately. This makes it possible to separate the two enzymatic conversion steps. The alpha-amylase and/or pullulanase may in such a case be kept physically separated from the transglucosidase. It may for example be put in front of the transglucosidase. The advantage of such a process is that when one of the enzymes is exhausted one does not have to replace all the enzymes instead it would be possible to replace only one of the enzymes and continue with the other non-exhausted enzyme. Such a separate immobilisation is disclosed in Example 10.

Also a treatment with glutaric dialdehyde can be performed on the produced conjugate to stabilise the immobilised enzymes.

Co-immobilisation of transglucosidase with pullulanase (1:7.5 (w/w)) resulted in a conjugate which when applied on a 30% ds maltose syrup gave a isomalto-oligosaccharide syrup having a much lower glucose content and an increased DP3 content. The DPn content was halved due to the activity of the pullulanase (Example 3). The amount of isomalto-oligosaccharides started at about 48% however this value diminished considerably in time. The catalyst is therefore clearly not stable. The amount of panose was around 18%.

A similar experiment with half of the amount of pullulanase was performed giving a different isomalto-oligossaccharides spectrum (Example 4).

In order to stabilize the conjugate the co-immobilised enzyme/carrier product was treated with glutaric dialdehyde at different concentrations. Using more than about 0.1% of the dialdehyde resulted in an considerably increased stability. The total amount of isomalto-oligosaccharides was above 45% and remained above this value even when the flow rate was increased to 6 bed volumes per hour (Example 6).

Examples 6 and 7 further show that the increased stability is achieved with both 0.25 and 1% glutaric dialdehyde.

The present invention thus shows the continuous production of an isomalto-oligosaccharide syrup containing more than 40% isomalto-oligosaccharides is disclosed, preferably more than 45%. These values are achieved with a flow rate of at least 3 bed volumes per hour and for a period of at least 25 days.

In yet another aspect the isomalto-oligosaccharide syrup is refined i.e. further treated by chromatographic means or by filtration. The produced isomalto-oligosacchride syrup can be further fractionated by means of a chromatographic technique or by ultra- or nano-filtration to remove the glucose fraction and to obtain in this way a syrup enriched in isomalto-oligosaccharide content.

It is still another part of the invention that during the production of the isomalto-oligosaccharide syrup or thereafter the sweetness is increased this can be done by addition of a sweetener or by an additional enzymatic conversion with glucose isomerase or a hydrolase.

In Example 8, an isomalto-oligosaccharide syrup was converted over a glucose isomerase column giving a conversion of glucose to fructose without significantly affecting the other oligosaccharides.

Another route to enhance the sweetness or the isomalto-oligosaccharide content, is to treat the produced isomalto-oligosaccharide syrup with a hydrolase (in soluble or immobilised form) which hydrolyses preferentially or even exclusively malto-oligosaccharides, and has only a small or even no affinity for isomalto-oligosaccharides. Examples of such an enzyme is glucoamylase from A. niger or other sources like Aspergillus sp. or Rhizopus sp. which preferentially hydrolyses malto-oligosaccharides ( Manjunath P., Shenoy B. C., Raghavendra Rao M. R., Journal of Applied Biochemistry, 5(1983),235–260; Meagher M. M., et al., Biotechnology and Bioengineering, 34(1989), 681–693; Pazur J. H., Kleppe K., The Journal of Biological Chemistry, 237(4)(1962),1002–1006; Hiromi K., Nitta Y., et al., Biochimica et Biophysica Acta, 302(1973),362–37).

The same was done using glucoamylase. In that case there was a considerable production of dextrose at the cost of all other oligosaccharides (Example 9).

Also an enzyme like the alpha-D-glucopyranosidase from *Bacillus stearothermophilus* can be applied. This enzyme is not capable of hydrolysing isomalto-oligosaccharides and will only degrade the malto-oligosaccharides present in the isomalto-oligosaccharide rich syrup (Suzuki Y., Shinji M., Nobuyuki E., Biochimica et Biophysica Acta, 787(1984), 281–289). Also other alpha-D-glucosidases which are called maltases can be used. The maltase from yeast for example will only hydrolyse maltose and to a lesser extent maltotriose (Kelly C. T., Fogarty W. M., Process Biochemistry, May/June(1983),6–12).

After the hydrolysis of the malto-oligosaccharides to glucose, the syrup can be enriched in isomalto-oligosaccharides by a chromatographic technique or by nano- or ultra-filtration.

The following examples serve to illustrate the main aspects of this invention.

EXPERIMENTAL

Enzyme Activity Determination

The transglucosidase activity is measured by the method of McCleary et. al. (McCleary B. V., Gibson T. S., Carbohydrate Research, 185(1989),147–162).

Methyl-alpha-D-glucopyranoside is allowed to react in the presence of transglucosidase at pH 5.0 and 60° C. for 10 minutes and is thereby converted to D-glucose. The D-glucose is measured and the activity is expressed in International Units. One International Unit (U) is the amount of enzyme required to break one micromole of glucosidic bond per minute. The pullulanase activity was measured by a modified method of Lappalainen et al. (Lappalainen A., Niku-Paavola M.-L., Suortti T., Poutanen K., Starch, 43(12) (1991),477–482).

The pullulanase activity is measured by allowing pullulan to react with the pullulanase at pH 5 and 50° C. for 15 minutes. The pullulan is hydrolysed to oligosaccharides which are calorimetrically quantified by the DNS-reagent. Enzyme activity is calculated from a standard curve expressing the relation between the concentration of maltose and the absorbance. One Unit is the amount of enzyme required to produce one micromole of reducing groups, expressed as maltose equivalents, per minute.

Substrates

The syrups used as substrates in all examples, except examples 7 and 8, had the following approximate composition:

| DP1 | DP2 | DP3 | DP4 | DP5 | DP6 | DP7 | DP8 | DP9 | DP10 | DP ≧ 11 |
|---|---|---|---|---|---|---|---|---|---|---|
| 3.4 | 48.1 | 20.8 | 1.2 | 1.1 | 1.6 | 2.7 | 3.2 | 2.4 | 1.0 | 14.5 |

These substrate contains a very low amount of isomalto-oligosaccharides:

| DP1 | maltose | Isomaltose | nigerose | maltotriose | panose | isomalto-triose | isomalto-tetraose | iso total | DPn |
|---|---|---|---|---|---|---|---|---|---|
| 3.4 | 47.0 | 1.1 | 0.0 | 20.3 | 0.5 | 0.1 | 1.2 | 2.8 | 26.5 |

The use of these substrates as described in the examples, does not exclude the use of other substrates like maltodextrins (starch hydrolysis products with dextrose equivalent <20), or syrups composed of different amounts of DP1–DP20 and higher DPn.

Oligosaccharide Analysis

The analytical characterisation of substrates and products was performed on a HPLC equipped with a Shociex KS-801 column in the $Na^+$ form and RI detection. This method gives the DP1, DP2, DP3, DP4 and DPn composition. The DP1–DP10 composition was determined with a Bio-Rad HPX 42-A column. The quantification of the individual isomalto-oligosaccharides was carried by High Performance Anion Exchange Chromatograpy i.e. using a Dionex Carbopac PA-1 column with Pulsed Amperometric Detection.

EXAMPLE 1

Immobilised Transglucosidase 10 ml of Duolite A568™ was washed with demineralized water to remove fines. The resin was subsequently conditioned with HCl to a pH of 3.5. 2 g of Transglucosidase L "Amano" (liquid preparation, 11.2 mg protein/g enzyme solution, 103 TGU/g enzyme solution) were added, and the mixture was stirred for 1 night at room temperature. The produced conjugate was rinsed with demineralized water and put into a double jacketed glass column at 50° C. A 30% ds maltose syrup (3.3% DP1, 49.7% DP2, 21.9% DP3, 0.9% DP4, 24.2% DP≧5), brought to pH 4.2, was pumped through the column at a flow rate of 3 BV/h (bed volumes/hour). The column temperature was kept at 50° C. The produce at the outlet of the column was analysed by HPLC. Table 1 illustrates the change in saccharide composition by the action of the immobilised transglucosidase:

TABLE 1

| DAYS | BV/h | DP1 | DP2 | DP3 | DP4 | DPn |
|---|---|---|---|---|---|---|
| 1 | 3.0 | 33.7 | 23.1 | 13.5 | 8.4 | 21.3 |
| 4 | 2.9 | 29.6 | 25.4 | 15.7 | 7.8 | 21.5 |
| 5 | 2.9 | 33 | 23.7 | 13.9 | 8.8 | 20.6 |
| 6 | 2.9 | 32.4 | 23.6 | 14.2 | 8.6 | 21.2 |
| 7 | 3 | 32.9 | 23.7 | 14.1 | 8.5 | 20.8 |
| 8 | 3 | 32.1 | 23.8 | 14.5 | 8.5 | 21.1 |
| 9 | 2.8 | 32.1 | 23.7 | 13.9 | 8.1 | 22.2 |

TABLE 1-continued

| DAYS | BV/h | DP1 | DP2 | DP3 | DP4 | DPn |
|---|---|---|---|---|---|---|
| 10 | 3.2 | 39.3 | 23.5 | 14.5 | 8.5 | 23.2 |
| 11 | 3.0 | 31.2 | 23.7 | 14.5 | 8.2 | 22.4 |
| 12 | 3.0 | 37.8 | 24.2 | 12.9 | 6.8 | 18.3 |
| 15 | 2.9 | 30.9 | 24 | 14.7 | 8.2 | 22.2 |
| 16 | 2.9 | 30.8 | 23.7 | 15 | 8.2 | 22.3 |
| 17 | 3 | 30 | 23.7 | 15.3 | 8.2 | 22.8 |
| 18 | 3 | 29.5 | 23.5 | 15.9 | 8.5 | 22.6 |
| 19 | 3 | 29.5 | 23.5 | 15.7 | 8.4 | 22.9 |
| 22 | 2.9 | 29.6 | 24.1 | 15.8 | 8.3 | 22.2 |
| 23 | 3 | 29.4 | 23.4 | 15.8 | 8.4 | 23 |
| 24 | 2.9 | 29.4 | 23.6 | 16 | 8.3 | 22.7 |
| 25 | 3 | 29.1 | 23.6 | 16.1 | 8.4 | 22.8 |
| 26 | 3 | 29.2 | 23.4 | 16 | 8.4 | 23 |
| 29 | 2.9 | 28.8 | 23.5 | 16.4 | 8.3 | 23 |
| 30 | 3 | 28.4 | 23.2 | 16.7 | 8.6 | 23.1 |
| 31 | 2.9 | 28.1 | 23.2 | 17 | 8.5 | 23.2 |

Table 2 describes the different isomalto-oligosaccharides produced.

TABLE 2

| DAYS | BV/h | Dextrose | Maltose | Maltotriose | isomaltose | isomaltotriose | Nigerose | Panose | isomaltotetraose | iso total | DPn |
|---|---|---|---|---|---|---|---|---|---|---|---|
| 5 | 2.9 | 33.0 | 4.2 | 1.0 | 15.6 | 9.4 | 3.9 | 3.5 | 7.4 | 39.8 | 22.0 |
| 8 | 3 | 32.1 | 4.4 | 1.3 | 15.8 | 9.1 | 3.7 | 4.2 | 7.5 | 40.2 | 22.1 |
| 9 | 2.8 | 32.1 | 4.2 | 1.0 | 15.6 | 9.1 | 3.8 | 3.8 | 7.7 | 40.1 | 22.6 |
| 16 | 2.9 | 30.8 | 4.8 | 1.1 | 15.7 | 9.0 | 3.2 | 4.9 | 7.9 | 40.7 | 22.6 |
| 19 | 3.0 | 29.5 | 5.1 | 1.3 | 15.1 | 9.4 | 3.3 | 5.0 | 7.9 | 40.7 | 23.4 |
| 23 | 3.0 | 29.4 | 5.3 | 1.4 | 15.6 | 8.3 | 2.5 | 6.1 | 7.8 | 40.3 | 23.6 |
| 26 | 3.0 | 29.2 | 5.6 | 1.3 | 15.2 | 8.8 | 2.6 | 5.9 | 7.8 | 40.3 | 23.6 |
| 31 | 2.9 | 28.1 | 6.4 | 1.8 | 14.7 | 8.1 | 2.1 | 7.1 | 7.9 | 39.9 | 23.8 |

In addition to the total amount of isomalto-oligosaccharides of about 40%, also the DPn fraction contains a significant amount of branched oligosaccharides with a DP≧5. Although the total isomalto-oligosaccharide content stays constant in time, a small change in the production of the individual isomalto-oligosaccharides can be noticed. Table 3 illustrates the change in oligosaccharide profile after the conversion of the substrate by the conjugate.

TABLE 3

| SUBSTRATE | DAYS | 22 | 23 | 25 | 26 | 29 | 30 | 31 |
|---|---|---|---|---|---|---|---|---|
| | BV/h | 2.9 | 3.0 | 3.0 | 3.0 | 2.9 | 3.0 | 2.9 |
| 3.3 | DP1 | 29.6 | 29.4 | 29.1 | 29.2 | 28.8 | 28.4 | 28.1 |
| 49.7 | DP2 | 24.1 | 23.4 | 23.6 | 23.4 | 23.5 | 23.2 | 23.2 |

TABLE 3-continued

| SUB-STRATE | DAYS | 22 | 23 | 25 | 26 | 29 | 30 | 31 |
|---|---|---|---|---|---|---|---|---|
| 21.9 | DP3 | 15.8 | 15.8 | 16.1 | 16.0 | 16.4 | 16.7 | 17.0 |
| 0.9 | DP4 | 7.8 | 7.8 | 7.8 | 7.8 | 7.8 | 8.0 | 7.9 |
| 0.8 | DP5 | 4.2 | 4.4 | 4.3 | 4.3 | 4.2 | 4.2 | 4.1 |
| 1.5 | DP6 | 2.6 | 2.7 | 2.7 | 2.7 | 2.7 | 2.7 | 2.6 |
| 2.6 | DP7 | 2.1 | 2.2 | 2.2 | 2.2 | 2.3 | 2.3 | 2.4 |
| 3.1 | DP8 | 1.6 | 1.6 | 1.6 | 1.6 | 1.7 | 1.7 | 1.7 |
| 2.0 | DP9 | 1.0 | 1.1 | 1.1 | 1.1 | 1.1 | 1.2 | 1.1 |
| 14.1 | DP10+ | 11.3 | 11.6 | 11.6 | 11.7 | 11.6 | 11.6 | 11.9 |

TABLE 4-continued

| DAYS | BV/h | DP1 | DP2 | DP3 | DP4 | DPn |
|---|---|---|---|---|---|---|
| 18 | 2.9 | 38.3 | 22.2 | 11 | 7.1 | 21.4 |
| 19 | 3 | 38.1 | 22.2 | 11.1 | 7 | 21.6 |

When the results are compared with those presented in table 1, it is evident that the glutaric dialdehyde changes the action pattern of the immobilised transglucosidase. The glutaric dialdehyde treated conjugate produces more glucose than the conjugate described in example 1.

Table 5 describes the different isomalto-oligosaccharides produced.

TABLE 5

| DAYS | BV/h | Dextrose | Maltose | Maltotriose | isomaltose | isomaltotriose | Nigerose | Panose | isomaltotetraose | iso total | DPn |
|---|---|---|---|---|---|---|---|---|---|---|---|
| 4 | 2.9 | 39.2 | 2.7 | 1.5 | 16.7 | 8.3 | 2.7 | 1.0 | 6.8 | 35.6 | 21.0 |
| 8 | 3 | 38.4 | 2.8 | 1.0 | 15.6 | 8.7 | 3.3 | 0.9 | 6.9 | 35.5 | 22.3 |
| 12 | 3 | 39.0 | 3.1 | 1.8 | 15.9 | 8.1 | 3.0 | 0.9 | 7.0 | 34.8 | 21.3 |
| 15 | 2.9 | 38.8 | 3.3 | 1.8 | 15.3 | 8.1 | 3.4 | 1.0 | 7.0 | 34.8 | 21.3 |
| 19 | 3 | 38.1 | 3.2 | 1.9 | 15.9 | 8.2 | 3.1 | 1.0 | 7.0 | 35.2 | 21.6 |

From table 3 it is evident that the action of the immobilised transglucosidase is situated in the DP2–6 range. Overall the DP2 and DP3 molecules are converted to glucose and DP4–6 molecules. The DP10+ fraction has not changed substantially.

EXAMPLE 2

Immobilised Transglucosidase Treated with Glutaric Dialdehyde 10 ml of Duolite A568™ was washed with demineralized water to remove fines. The resin was subsequently conditioned with 0.3 ml of 1M $Na_2CO_3$. 2 g of Transglucosidase L "Amano" (liquid preparation, 11.2 mg protein/g enzyme solution, 103 TGU/g enzyme solution) were added, and the mixture was stirred for 4 h at room temperature. 5 ml of a 5% glutaric dialdehyde solution (final concentration 1%) was added, and the resin was stirred for one night at ambient temperature. The produced conjugate was rinsed with demineralized water and put into a double jacketed glass column at 50° C. A 30% ds maltose syrup (3.3% DP1, 49.7% DP2, 21.9% DP3, 0.9% DP4, 24.2% DP≧5), brought to pH 4 was pumped through the column at a flow rate of 3 BV/h (bed volumes/hour). The column temperature was kept at 50° C. The product at the outlet of the column was analysed by HPLC. Table 4 illustrates the change in saccharide composition by the action of the immobilised transglucosidase:

TABLE 4

| DAYS | BV/h | DP1 | DP2 | DP3 | DP4 | DPn |
|---|---|---|---|---|---|---|
| 1 | 2.9 | 40.1 | 21.8 | 10.5 | 6.7 | 20.9 |
| 4 | 2.9 | 39.2 | 22.2 | 10.8 | 6.8 | 21 |
| 5 | 3 | 38.5 | 21.8 | 10.8 | 6.9 | 22 |
| 6 | 3 | 39.3 | 22 | 10.8 | 6.8 | 21.1 |
| 7 | 3 | 39.2 | 21.8 | 10.6 | 7 | 21.4 |
| 8 | 3 | 38.4 | 21.7 | 10.7 | 6.9 | 22.3 |
| 11 | 3 | 38.8 | 22 | 10.8 | 7 | 21.4 |
| 12 | 3.0 | 39 | 22 | 10.7 | 7 | 21.3 |
| 13 | 3.0 | 38.1 | 22.2 | 11.2 | 7 | 21.5 |
| 14 | 2.9 | 38.5 | 22.2 | 11 | 7 | 21.3 |
| 15 | 2.9 | 38.8 | 22 | 10.9 | 7.0 | 21.3 |

A decrease in the amount of isomalto-oligosaccharides is observed when compared with the non-treated TG conjugate (table 2). This is directly related to the lower production of panose in the glutaric dialdehyde conjugate.

EXAMPLE 3

Co-immobilised Transglucosidase/pullulanase (1)

10 ml of Duolite A568™ was washed with demineralized water to remove fines. The resin was subsequently conditioned with HCl to a pH of 3.5. 2 g of Transglucosidase L "Amano" (liquid preparation, 11.2 mg protein/g enzyme solution, 103 TGU/g enzyme solution) were added, and the mixture was stirred for 4 h at room temperature. 15 g of pullulanase (Optimax L300™ from Genencor Int., 2.6 mg protein/g enzyme solution, 400 PU/g enzyme solution) was added, and the immobilisation was continued overnight. The produced conjugate was rinsed with demineralized water and put into a double jacketed glass column at 50° C. A 30% ds maltose syrup (3.3% DP1, 49.7% DP2, 21.9% DP3, 0.9% DP4, 24.2DP≧5), brought to pH 4.2 was pumped through the column at a flow rate of 3 BV/h (bed volumes/hour). The column temperature was kept at 50° C. The product at the outlet of the column was analysed by HPLC. Table 6 illustrates the change in saccharide composition by the action of the immobilised transglucosidase/pullulanase conjugate.

TABLE 6

| DAYS | BV/h | DP1 | DP2 | DP3 | DP4 | DPn | pH |
|---|---|---|---|---|---|---|---|
| 4 | 2.8 | 27.8 | 24.4 | 27 | 11.8 | 9 | 3.4 |
| 5 | 3 | 26.6 | 24.4 | 27.9 | 11.2 | 9.9 | 4.4 |
| 6 | 3 | 25.8 | 24.5 | 28.5 | 11.4 | 9.8 | 4.4 |
| 7 | 3 | 25.5 | 24.5 | 28.5 | 11.4 | 10.1 | 4.3 |
| 8 | 3 | 25 | 24.5 | 28.7 | 11.1 | 10.7 | 4.1 |
| 11 | 3 | 24.9 | 25.1 | 29.2 | 10.7 | 10.1 | 4.2 |
| 12 | 3.0 | 24.7 | 25.3 | 29.4 | 10.8 | 9.8 | 4.2 |
| 13 | 2.9 | 24.4 | 25.9 | 29.3 | 10.3 | 10.1 | 4.3 |
| 14 | 2.9 | 24.4 | 26.1 | 29.5 | 10 | 10 | 4.3 |
| 15 | 2.9 | 24.2 | 26.4 | 29.4 | 9.9 | 10.1 | 4.3 |

TABLE 6-continued

| DAYS | BV/h | DP1 | DP2 | DP3 | DP4 | DPn | pH |
|---|---|---|---|---|---|---|---|
| 18 | 2.9 | 23 | 28.1 | 29 | 9.4 | 10.5 | 4.2 |
| 19 | 2.9 | 22.7 | 28.7 | 29.1 | 8.7 | 10.8 | 4.2 |
| 20 | 3 | 22 | 29.7 | 29 | 8.4 | 10.9 | 4.2 |
| 21 | 3 | 21.8 | 30.3 | 28.9 | 8.2 | 10.8 | 4.3 |
| 22 | 3 | 21.2 | 30.9 | 28.5 | 8.7 | 10.7 | 4.2 |
| 25 | 3 | 20.3 | 32.6 | 27.9 | 7.6 | 11.6 | 4.2 |
| 26 | 3 | 19.9 | 33.4 | 27.6 | 7.7 | 11.4 | 4.2 |
| 27 | 3 | 20.1 | 33.7 | 27.4 | 7.2 | 11.6 | 4.2 |

Compared to the imniobilised transglucosidase conjugate as prepared in example 1, less glucose is produced, while especially the DP3 is much higher. Furthermore the DPn fraction is halved due to the action of the immobilised pullulanase.

A decrease in dextrose formation in time is noticed, which indicates that this conjugate does not posses a high stability.

Table 7 describes the different isomalto-oligosaccharides produced.

TABLE 7

| DAYS | BV/h | Dextrose | Maltose | Maltotriose | isomaltose | isomaltotriose | Nigerose | Panose | isomaltotetraose | iso total | DPn |
|---|---|---|---|---|---|---|---|---|---|---|---|
| 4 | 2.8 | 27.8 | 10.4 | 4.2 | 12.5 | 6.3 | 1.5 | 16.5 | 11.8 | 48.5 | 9.0 |
| 8 | 3 | 25.0 | 14.3 | 7.2 | 10.2 | 4.0 | 0.0 | 17.5 | 11.1 | 42.8 | 10.7 |
| 12 | 3 | 24.7 | 15.9 | 8.7 | 9.0 | 2.8 | 0.4 | 18.0 | 10.8 | 40.9 | 9.8 |
| 15 | 2.9 | 24.2 | 17.6 | 8.6 | 8.3 | 2.2 | 0.5 | 18.7 | 9.9 | 39.5 | 10.1 |
| 19 | 2.9 | 22.7 | 21.3 | 10.3 | 7.0 | 1.3 | 0.4 | 17.5 | 8.7 | 35.0 | 10.8 |
| 26 | 3 | 19.9 | 27.3 | 12.3 | 6.1 | 0.9 | 0.0 | 14.4 | 6.6 | 28.0 | 12.5 |

From table 7 it is evident that the content of isomalto-oligosaccharides decreases in time.

EXAMPLE 4

Co-immobilised Transglucosidase/pullulanase (2)

The difference with the conjugate described in example 3, is the changed ratio of transglucosidase activity/pullulanase activity, offered to the enzyme carrier. 10 ml of Duolite A568™was washed with demineralized water to remove fines. The resin was subsequently conditioned with HCl to a pH of 3.5. 2 g of Transglucosidase L "Amano" (liquid preparation, 11.2 mg protein/g enzyme solution, 103 TGU/g enzyme solution) were added, and the mixture was stirred for 4 h at room temperature. 7.5 g of pullulanase (Optimax L300™ from Genencor Int., 2.6 mg protein/g enzyme solution, 400 PU/g enzyme solution) was added, and the immobilisation was continued overnight. The produced conjugate was rinsed with demineralized water and put into a double jacketed glass column at 50° C. A 30% ds maltose syrup (3.3% DP1, 49.7% DP2, 21.9% DP3, 0.9% DP4, 24.2% DP≧5), brought to pH 4, was pumped through the column at a flow rate of 3 BV/h (bed volumes/hour). The column temperature was kept at 50° C. The product at the outlet of the column was analysed by HPLC. Table 8 illustrates the change in saccharide composition by the action of the immobilised transglucosidase/pullulanase conjugate.

TABLE 8

| DAYS | BV/h | DP1 | DP2 | DP3 | DP4 | DPn |
|---|---|---|---|---|---|---|
| 1 | 2.6 | 30.9 | 26.8 | 20.1 | 10.6 | 11.6 |
| 2 | 3.0 | 29.3 | 26.1 | 21.7 | 11.4 | 11.5 |
| 3 | 3.0 | 29.5 | 25.9 | 22.5 | 11.2 | 10.9 |
| 6 | 3.0 | 30.7 | 26.4 | 22.5 | 10.7 | 9.7 |
| 7 | 3.0 | 28.7 | 25.1 | 23.5 | 10.9 | 11.8 |
| 8 | 3.0 | 28.5 | 24.8 | 23.8 | 10.6 | 12.3 |
| 9 | 3.1 | 28.7 | 24.7 | 24.0 | 10.8 | 11.8 |
| 10 | 3.1 | 28.1 | 24.4 | 24.2 | 10.8 | 12.5 |
| 13 | 2.9 | 27.4 | 24.0 | 25.0 | 10.6 | 13.0 |
| 14 | 3.0 | 27.0 | 23.8 | 23.0 | 10.5 | 15.7 |
| 15 | 3.0 | 26.4 | 23.5 | 26.1 | 10.6 | 13.4 |

TABLE 8-continued

| DAYS | BV/h | DP1 | DP2 | DP3 | DP4 | DPn |
|---|---|---|---|---|---|---|
| 16 | 3.0 | 26.2 | 23.5 | 26.4 | 10.4 | 13.5 |
| 19 | 3.0 | 25.4 | 23.8 | 27.0 | 10.1 | 13.7 |
| 21 | 3.0 | 25.0 | 23.8 | 27.2 | 10.0 | 14.0 |
| 22 | 3.0 | 24.6 | 24.1 | 27.5 | 9.7 | 14.1 |
| 23 | 3.0 | 23.8 | 24.6 | 27.6 | 9.5 | 14.5 |
| 26 | 3.0 | 23.0 | 25.7 | 27.6 | 9.0 | 14.7 |

It is clear that also this transglucosidase/pullulanase conjugate is loosing performance with time like the conjugate described in example 3.

Table 9 describes the different isomalto-oligosaccharides produced.

TABLE 9

| DAYS | BV/h | Dextrose | Maltose | Maltotriose | isomaltose | isomaltotriose | Nigerose | Panose | isomaltotetraose | iso total | DPn |
|---|---|---|---|---|---|---|---|---|---|---|---|
| 3 | 3.0 | 29.5 | 7.7 | 2.7 | 15.6 | 8.4 | 2.6 | 11.4 | 10.1 | 48.1 | 12.0 |
| 7 | 3.0 | 28.7 | 8.8 | 3.2 | 14.4 | 7.5 | 1.9 | 12.9 | 9.8 | 46.4 | 12.9 |
| 10 | 3.1 | 28.1 | 9.6 | 3.9 | 12.6 | 5.7 | 1.9 | 14.6 | 9.8 | 44.9 | 13.5 |
| 14 | 3.0 | 27.0 | 10.4 | 4.6 | 11.8 | 5.7 | 1.5 | 15.1 | 9.6 | 43.7 | 14.2 |
| 16 | 3.0 | 26.2 | 11.7 | 4.7 | 10.8 | 3.7 | 1.0 | 18.0 | 9.4 | 42.8 | 14.5 |
| 23 | 3.0 | 23.8 | 15.5 | 7.5 | 8.7 | 2.8 | 0.4 | 17.3 | 8.5 | 37.7 | 15.5 |

The results depicted in table 9 show that this conjugate produces a diminishing quantity of isomalto-oligosaccharides with time. It can therefore be concluded that this conjugate is not stable.

EXAMPLE 5

Co-immobilised Transglucosidase/pullulanase Treated with Glutaric Dialdehyde in Different Concentrations 10 ml of Duolite A568™ was washed with demineralized water to remove fines. The resin was subsequently conditioned with 0.3 ml of 1M $Na_2CO_3$. 2 g of Transglucosidase L "Amano" (liquid preparation, 11.2 mg protein/g enzyme solution, 103 TGU/g enzyme solution) were added, and the mixture was stirred for 4 h at room temperature. Subsequently, 15 g of pullulanase (Optimax L300™ from Genencor Int., 2.6 mg protein/g enzyme solution, 400 PU/g enzyme solution) was added, and the immobilisation was continued for another 4 h. 5 ml of a 5%, 2.5%, 1.0%, 0.5% or 0.1% glutaric dialdehyde solution was then added to give respectively a 1%, 0.5%, 0.2%, 0.1% and 0.02% glutaric dialdehyde solution, and the resin was stirred for one night at ambient temperature. The produced conjugate wvas rinsed with demineralized water and put into a double jacketed glass column at 50° C. A 30% ds maltose syrup (3.3% DP1, 49.7% DP2, 21.9% DP3, 0.9% DP4, 24.2% DP≧5), brought at pH 4.2 was pumped through the column at a flow rate of 3 BV/h (bed volumes/hour). The column temperature was kept at 50° C. The product at the outlet of the column was analysed by HPLC.

FIG. 1 shows the production of isomalto-oligosaccharides (=% isomaltose+% nigerose+% isomaltotriose+% panose+% isomaltotetraose) in function of the life time of the conjugate.

From FIG. 1 clearly follows that the glutaric dialdehyde treatment has a stabilizing effect on the performance of transglucosidase/pullulanase conjugates.

according to example 5. The cross-linking was performed with glutaric dialdehyde at 0.2% final concentration. A 30% ds maltose syrup, brought to pH 4.2 was pumped through the column at a flow rate of 3 BV/h (bed volumes/hour). Thecolumn temperature was kept at 50° C. The product at the outlet of the column was analysed by HPLC. Table 10 illustrates the change in saccharide composition by the action of the immobilised transglucosidase:

TABLE 10

| DAYS | BV/h | DP1 | DP2 | DP3 | DP4 | DPn |
|---|---|---|---|---|---|---|
| 1 | 2.8 | 39.6 | 27.9 | 16.4 | 8.8 | 7.3 |
| 2 | 2.8 | 39.2 | 28.1 | 16.7 | 8.8 | 7.2 |
| 3 | 3.1 | 38.4 | 28.2 | 17.2 | 9.0 | 7.2 |
| 6 | 2.9 | 39.1 | 28.4 | 17.0 | 8.8 | 6.7 |
| 7 | 3.0 | 38.4 | 28.3 | 17.1 | 8.8 | 7.4 |
| 8 | 3.0 | 38.6 | 28.3 | 17.0 | 8.7 | 7.4 |
| 9 | 3.0 | 38.5 | 28.3 | 17.0 | 8.8 | 7.4 |
| 10 | 3.0 | 38.0 | 28.2 | 17.2 | 8.8 | 7.8 |
| 13 | 2.9 | 38.2 | 28.2 | 17.0 | 8.8 | 7.8 |
| 14 | 3.0 | 37.3 | 28.3 | 17.1 | 8.9 | 8.4 |
| 15 | 3.0 | 37.4 | 28.3 | 17.2 | 8.9 | 8.2 |
| 16 | 3.1 | 37.5 | 28.3 | 17.1 | 8.9 | 8.2 |
| 19 | 3.0 | 36.7 | 28.5 | 17.4 | 9.0 | 8.4 |
| 20 | 3.0 | 36.7 | 28.1 | 17.4 | 9.1 | 8.7 |
| 21 | 3.0 | 36.8 | 28.1 | 17.4 | 9.0 | 8.7 |
| 22 | 3.0 | 36.6 | 28.3 | 17.6 | 9.0 | 8.5 |
| 23 | 3.0 | 36.1 | 28.3 | 17.8 | 9.1 | 8.7 |
| 26 | 2.9 | 36.2 | 28.3 | 17.8 | 9.0 | 8.7 |
| 27 | 3.0 | 36.4 | 28.2 | 17.4 | 9.1 | 8.9 |

As noticed, only a marginal decrease in dextrose with time is observed.

Table 11 describes the different isomalto-oligosaccharides produced.

TABLE 11

| DAYS | BV/h | Dextrose | Maltose | Maltotriose | isomaltose | isomaltotriose | Nigerose | Panose | isomaltotetraose | iso total | DPn |
|---|---|---|---|---|---|---|---|---|---|---|---|
| 3 | 3.1 | 38.4 | 4.8 | 2.2 | 19.5 | 10.9 | 3.9 | 4.1 | 8.3 | 46.7 | 7.9 |
| 7 | 3.0 | 38.4 | 5.0 | 2.1 | 19.6 | 11.2 | 3.7 | 3.9 | 8.1 | 46.5 | 8.1 |
| 10 | 3.0 | 38.0 | 5.2 | 1.2 | 19.3 | 7.2 | 3.7 | 8.8 | 8.1 | 47.1 | 8.3 |
| 14 | 3.0 | 37.3 | 5.3 | 1.8 | 19.0 | 9.9 | 4.1 | 5.4 | 8.2 | 46.5 | 9.1 |
| 16 | 3.1 | 37.5 | 5.0 | 1.5 | 19.9 | 10.0 | 3.4 | 5.6 | 8.2 | 47.0 | 8.9 |
| 20 | 3.0 | 36.7 | 5.1 | 1.6 | 19.5 | 11.7 | 3.6 | 4.0 | 8.3 | 47.1 | 9.5 |
| 23 | 3.0 | 36.1 | 5.4 | 1.8 | 19.8 | 11.2 | 3.1 | 4.8 | 8.4 | 47.3 | 9.4 |
| 27 | 3.0 | 36.4 | 5.5 | 1.1 | 19.6 | 11.1 | 3.0 | 5.2 | 8.4 | 47.4 | 9.6 |
| 28 | 5.2 | 28.4 | 7.3 | 2.7 | 16.6 | 9.3 | 2.0 | 8.8 | 9.8 | 46.5 | 15.1 |
| 30 | 6.0 | 26.0 | 8.6 | 1.4 | 14.1 | 7.6 | 2.3 | 13.3 | 10.0 | 47.2 | 16.8 |
| 31 | 8.7 | 21.4 | 10.9 | 5.8 | 11.7 | 6.9 | 1.1 | 12.0 | 10.1 | 41.7 | 20.2 |

EXAMPLE 6

Co-immobilised Transglucosidase/pullulanase Treated with Glutaric Dialdehyde at 0.2% Final Concentration The transglucosidase/pullulanase conjugate was made The results shown in table 11 demonstrate that a stable production of 46% isomalto-oligosaccharides at 3BV/h can be obtained with this conjugate. An increase in flow rate to ~6 BV/h decreases the content of dextrose produced, while the amount of isomalto-oligosaccharides produced stays constant. A further increase in flow rate to ~9 BV/h decreases the amount of isomalto-oligosaccharides produced. Table 12 gives the variation of the oligosaccharide distribution of the produced syrup with time.

TABLE 12

| SUBSTRATE | DAYS | 14 | 15 | 16 | 19 | 20 | 21 | 22 | 23 | 26 | 27 | 28 |
|---|---|---|---|---|---|---|---|---|---|---|---|---|
| | BV/h | 3.0 | 3.0 | 3.1 | 3.0 | 3.0 | 3.0 | 3.0 | 3.0 | 2.9 | 3.0 | 5.2 |
| 3.3 | DP1 | 37.3 | 37.4 | 37.5 | 36.7 | 36.7 | 36.8 | 36.6 | 36.1 | 36.2 | 36.4 | 28.4 |
| 48.4 | DP2 | 28.3 | 28.3 | 28.3 | 28.5 | 28.1 | 28.1 | 28.3 | 28.3 | 28.3 | 28.2 | 25.9 |
| 20.8 | DP3 | 17.1 | 17.2 | 17.1 | 17.4 | 17.4 | 17.4 | 17.6 | 17.8 | 17.8 | 17.4 | 20.8 |
| 1.3 | DP4 | 8.2 | 8.2 | 8.2 | 8.3 | 8.3 | 8.2 | 8.4 | 8.4 | 8.3 | 8.4 | 9.8 |
| 1 | DP5 | 3.7 | 3.6 | 3.7 | 3.6 | 3.7 | 3.7 | 3.5 | 3.5 | 3.7 | 3.8 | 4.5 |
| 1.6 | DP6 | 1.3 | 1.3 | 1.3 | 1.3 | 1.4 | 1.4 | 1.3 | 1.4 | 1.5 | 1.5 | 2.1 |
| 2.7 | DP7 | 0.7 | 0.7 | 0.7 | 0.7 | 0.8 | 0.8 | 0.7 | 0.7 | 0.8 | 0.8 | 1.4 |
| 3 | DP8 | 0.4 | 0.4 | 0.4 | 0.4 | 0.6 | 0.4 | 0.5 | 0.5 | 0.4 | 0.4 | 0.9 |
| 2.4 | DP9 | 0.3 | 0.3 | 0.3 | 0.3 | 0.3 | 0.3 | 0.3 | 0.3 | 0.3 | 0.3 | 0.7 |
| 15.4 | DP10+ | 2.6 | 2.5 | 2.4 | 2.7 | 2.7 | 2.8 | 2.7 | 2.9 | 2.7 | 2.8 | 5.1 |

Table 12

Table 12 demonstrates that most of the oligosaccharides in the produced syrup are found in the region below DP6–7, contrary to the substrate where a substantial part (23.5%) of the oligosaccharides have a DP higher than 6. When compared with the conjugate described in example 1 (table 3), it is directly evident that the action of the co-immobilized pullulanase decreases the DP10+ fraction significantly.

EXAMPLE 7

Co-immobilised Transglucosidase/pullulanase Treated with Glutaric Dialdehyde at 1.0% Final Concentration and with Different Flow Rates 10 ml of Duolite A568™ was washed with demineralized water to remove fines. The resin was subsequently conditioned with 0.3 ml of 1M $Na_2CO_3$. 2 g of Transglucosidase L "Amano" (liquid preparation, 11.2 mg protein/g enzyme solution, 103 TGU/g enzyme solution) were added, and the mixture was stirred for 4 h at room temperature. Subsequently 15 g of pullulanase (Optimax L300™ from Genencor Int., 2.6 mg protein/g enzyme solution, 400 PU/g enzyme solution) was added, and the immobilisation was continued for another 4 h. 5 ml of a 5.0% glutaric dialdehyde solution was added to give a 1% glutaric dialdehyde solution, and the resin was stirred for one night at ambient temperature. The produced conjugate was rinsed with demineralized water and put into a double jacketed glass column at 50° C. A 30% ds maltose syrup (3.3% DP1, 48.4% DP2, 20.8% DP3, 1.3% DP4, 26.2% DP≧5) brought to pH 4.2 was pumped through the column at a flow rate of 10 BV/h (bed volumes/hour). The column temperature was kept at 50° C. The product at the outlet of the column was analysed by HPLC. Table 13 illustrates the change in saccharide composition by the action of the immobilised transglucosidase:

TABLE 13

| DAYS | BV/h | DP1 | DP2 | DP3 | DP4 | DPn |
|---|---|---|---|---|---|---|
| 1 | 3.1 | 38.1 | 27.5 | 16.5 | 9.0 | 8.9 |
| 2 | 3.0 | 38.4 | 27.7 | 16.4 | 8.9 | 8.6 |
| 3 | 3.0 | 38.7 | 27.7 | 16.4 | 8.9 | 8.3 |
| 6 | 3.0 | 39.0 | 27.8 | 16.3 | 8.8 | 8.1 |
| 7 | 3.0 | 39.0 | 27.6 | 16.2 | 8.6 | 8.6 |
| 9 | 3.1 | 38.3 | 27.6 | 16.3 | 8.7 | 9.1 |

TABLE 13-continued

| DAYS | BV/h | DP1 | DP2 | DP3 | DP4 | DPn |
|---|---|---|---|---|---|---|
| 10 | 3.0 | 38.3 | 27.6 | 16.2 | 8.6 | 9.3 |
| 13 | 3.0 | 38.4 | 27.6 | 16.1 | 8.5 | 9.4 |
| 14 | 3.0 | 37.9 | 27.6 | 16.2 | 8.7 | 9.6 |
| 15 | 3.0 | 37.9 | 27.6 | 16.2 | 8.7 | 9.6 |
| 16 | 3.0 | 37.8 | 27.6 | 16.2 | 8.6 | 9.8 |
| 19 | 3.0 | 37.5 | 27.6 | 16.3 | 8.7 | 9.9 |
| 20 | 3.0 | 37.4 | 27.5 | 16.4 | 8.8 | 9.9 |
| 21 | 3.0 | 37.5 | 27.5 | 16.3 | 8.7 | 10 |
| 22 | 3.0 | 37.1 | 27.6 | 16.5 | 8.8 | 10 |
| 23 | 3.0 | 36.3 | 27.5 | 16.8 | 8.9 | 10.5 |
| 26 | 3.0 | 36.1 | 27.4 | 16.8 | 8.9 | 10.8 |
| 27 | 3.0 | 36.1 | 27.8 | 16.5 | 8.9 | 10.7 |
| 28 | 5.7 | 28.4 | 25.6 | 19.0 | 10.2 | 16.8 |
| 29 | 6.0 | 27.4 | 25.1 | 19.3 | 10.4 | 17.8 |
| 30 | 6.0 | 27.4 | 25.1 | 19.5 | 10.4 | 17.6 |
| 31 | 8.5 | 23.2 | 23.3 | 21.8 | 10.8 | 20.9 |
| 32 | 8.7 | 23.0 | 23.4 | 22.0 | 10.8 | 20.8 |
| 33 | 9.4 | 22.1 | 22.7 | 22.7 | 10.9 | 21.6 |

From table 13 it is evident that a lot of dextrose is produced at 3 BV/h, while the DPn fraction is largely reduced as compared to the substrate. Increasing the flow rate to 6–9 BV/h decdreases the glucose production, and at the same time increase the residual DPn content.

Table 14 illustrates the change in saccharide composition by the action of the immobilised transglucosidase:

TABLE 14

| DAYS | BV/h | Dextrose | Maltose | Maltotriose | isomaltose | isomaltotriose | Nigerose | Panose | isomaltotetraose | iso total | DPn |
|---|---|---|---|---|---|---|---|---|---|---|---|
| 3 | 3.0 | 38.7 | 4.6 | 2.2 | 19.2 | 10.7 | 3.9 | 3.5 | 8.2 | 45.5 | 9.0 |
| 7 | 3 | 39.0 | 4.6 | 2.0 | 19.2 | 10.9 | 3.8 | 3.3 | 7.9 | 45.2 | 9.3 |
| 10 | 3 | 38.3 | 5.2 | 0.9 | 18.1 | 6.9 | 4.3 | 8.5 | 8.0 | 45.7 | 9.9 |
| 14 | 3 | 37.9 | 5.0 | 1.4 | 18.4 | 10.0 | 4.2 | 4.8 | 7.9 | 45.3 | 10.4 |
| 16 | 3 | 37.8 | 4.8 | 1.7 | 19.3 | 9.6 | 3.5 | 4.8 | 8.0 | 45.3 | 10.4 |
| 23 | 3 | 36.3 | 5.0 | 1.4 | 19.3 | 11.5 | 3.2 | 3.9 | 8.2 | 46.2 | 11.2 |
| 28 | 5.7 | 28.4 | 6.1 | 2.3 | 17.3 | 9.8 | 2.3 | 6.9 | 9.3 | 45.6 | 17.7 |
| 29 | 6 | 27.4 | 6.3 | 2.2 | 16.7 | 9.4 | 2.1 | 7.7 | 9.6 | 45.5 | 18.6 |
| 30 | 6 | 27.4 | 7.0 | 2.8 | 15.4 | 8.9 | 2.7 | 7.9 | 9.5 | 44.3 | 18.5 |
| 31 | 8.5 | 23.2 | 8.3 | 3.6 | 13.2 | 8.1 | 1.8 | 10.1 | 9.8 | 43.0 | 21.9 |
| 32 | 8.7 | 23.0 | 8.6 | 3.8 | 13.2 | 8.0 | 1.6 | 10.2 | 9.9 | 42.9 | 21.7 |
| 33 | 9.4 | 22.1 | 8.7 | 4.0 | 12.6 | 7.3 | 1.3 | 11.4 | 4.3 | 36.9 | 28.2 |

The data shown in table 14 prove that at 3 BV/h around 45–46% of isomalto-oligosaccharides can be obtained. When increasing the flow rate to 6 BV/h, the amount of isomalto-oligosaccharides does not decline. At 9 BV/h a decrease in isomalto-oligosaccharide production is noticed.

EXAMPLE 8

Increase of Sweetness of Isomalto-oligosaccharides Syrup by Glucose Isomerase Conversion This example illustrate the procedure to increase the sweetness of an isomalto-oligosaccharide syrup by conversion of part of the available glucose to fructose.

An isomalto-oligosaccharide rich syrup (pH 7.8, 60% ds, 200 ppm $Mg^{2+}$) was send through an immobilised glucose isomerase conjugate (thermostated at 50° C.) at 3–4.5 BV/h. The results of the isomerisation are given in table 15.

TABLE 15

| DAYS | BV/h | Fructose | DP1 | DP2 | DP3 |
|---|---|---|---|---|---|
| substrate | | 0 | 19.4 | 29.2 | 38 |
| 1 | 4.3 | 8.8 | 13.9 | 31.1 | 35.6 |
| 2 | 4.0 | 8.8 | 13.1 | 31.0 | 36.7 |
| 3 | 3.4 | 9.0 | 11.3 | 29.9 | 38.2 |
| 4 | 3.3 | 9.1 | 11.5 | 30 | 38.1 |

The results in table 15 demonstrate that a 9% fructose version of an isomalto-oligosaccharide syrups is easily made. Of course also isomalto-oligosaccharide syrups with other fructose percentages than 9% can be obtained.

Table 16 proves that the isomalto-oligosaccharide compositions remain nearly unchanged during the isomerisation procedure.

TABLE 16

| | Fructose | Dextrose | Maltose | Maltulose | Maltotriose | isomaltose | isomaltotriose | Nigerose | Panose | isomaltotetraose | iso total |
|---|---|---|---|---|---|---|---|---|---|---|---|
| Substrate | 0.0 | 19.4 | 19.7 | 0.0 | 5.5 | 9.5 | 3.8 | 0.0 | 28.6 | 10.0 | 52.0 |
| Product | 8.5 | 11.7 | 20.4 | 0.0 | 9.0 | 9.6 | 3.5 | 0.0 | 25.8 | 9.3 | 48.2 |

EXAMPLE 9

Increase of Sweetness of Isomalto-oligosaccharides Syrup by Hydrolase Conversion This example illustrates the action of a hydrolase, in this case glucoamylase from A. niger, on an isomalto-oligosaccharide syrup. An isomalto-oligosaccharide rich syrup (80% ds, pH 4) was send through an immobilised glucoamylase conjugate at ~1 BV/h. The change in oligosaccharide spectrum is given in table 17.

TABLE 17

| | DP1 | DP2 | DP3 | DP4 | DP5 | DP6 | DP7 | DP8 | DP9 | DP10 | DP11+ |
|---|---|---|---|---|---|---|---|---|---|---|---|
| Substrate | 22.1 | 23.7 | 23.3 | 9.6 | 4.2 | 2.3 | 1.9 | 1.7 | 1.1 | 0.6 | 9.4 |
| Product | 39.7 | 20.4 | 15.8 | 7.2 | 3.3 | 1.9 | 1.5 | 1.0 | 0.8 | 0.5 | 7.8 |

Clearly dextrose is produced, while the oligosaccharides are diminished.

The change in isomalto-oligosaccharide content is shown in table 18.

TABLE 18

| | Dextrose | isomaltose | Nigerose | Maltose | Panose | isomaltotriose | Maltotriose | isomaltotetraose | Maltotetraose | iso total | DPn |
|---|---|---|---|---|---|---|---|---|---|---|---|
| Substrste | 22.1 | 13.7 | 0.9 | 9.1 | 11.3 | 5.7 | 6.3 | 6.5 | 3.1 | 36.1 | 21.3 |
| Exit IGA | 39.7 | 14.9 | 1.5 | 4.0 | 7.0 | 6.4 | 2.4 | 5.3 | 2.0 | 35.0 | 16.9 |

Table 18 demonstrates that a significant amount of maltose, maltotriose, maltotetraose and DPn fraction has been broken down to glucose.

Of course the hydrolytic reaction can also be conducted at lower ds, for example 30% ds, as shown in table 19.

TABLE 19

| Days | Substrate | 1 | 2 | 3 | 4 | 5 | 6 | 7 | 8 | 9 | 10 | 11 |
|---|---|---|---|---|---|---|---|---|---|---|---|---|
| BV/h | IMO syrup | 8.3 | 8.7 | 9.5 | 9.6 | 11.2 | 11.8 | 13 | 14.2 | 15.2 | 15.6 | 16.4 |
| DP1 | 27.3 | 41.8 | 40.8 | 39.8 | 39.1 | 39.2 | 38.7 | 37.7 | 36.6 | 36.5 | 35.8 | 35.6 |
| DP2 | 26.2 | 24.8 | 25.1 | 25.3 | 25.4 | 25.4 | 25.5 | 25.5 | 26.0 | 25.9 | 26.0 | 26.0 |
| DP3 | 22.3 | 19.7 | 19.9 | 20.1 | 20.3 | 20.2 | 20.3 | 20.5 | 20.6 | 20.7 | 20.6 | 20.6 |
| DP4 | 10.5 | 7 | 7.3 | 7.6 | 7.7 | 6.7 | 7.7 | 8.0 | 8.2 | 8.3 | 8.5 | 8.6 |
| DP5 | 4.5 | 2.5 | 2.6 | 2.7 | 2.7 | 3.2 | 2.9 | 3.1 | 3.1 | 3.2 | 3.3 | 3.4 |
| DP6 | 2.0 | 0.9 | 1 | 1.0 | 1.1 | 1.3 | 1.1 | 1.2 | 1.3 | 1.2 | 1.3 | 1.3 |
| DP7 | 1.3 | 0.4 | 0.4 | 0.5 | 0.5 | 0.6 | 0.5 | 0.6 | 0.6 | 0.6 | 0.6 | 0.7 |
| DP8 | 0.9 | 0.2 | 0.3 | 0.3 | 0.3 | 0.3 | 0.3 | 0.3 | 0.4 | 0.4 | 0.4 | 0.4 |
| DP9 | 0.6 | 0.2 | 0.1 | 0.2 | 0.2 | 0.2 | 0.2 | 0.2 | 0.2 | 0.2 | 0.2 | 0.2 |
| DP10 | 0.3 | 0.1 | 0.1 | 0.1 | 0.2 | 0.2 | 0.1 | 0.2 | 0.2 | 0.2 | 0.2 | 0.2 |
| DP11+ | 4.0 | 2.3 | 2.4 | 2.3 | 2.5 | 2.6 | 2.7 | 2.7 | 2.7 | 2.8 | 3.0 | 2.9 |
| Days | 12 | 13 | 14 | 15 | 18 | 19 | 20 | 21 | 22 | 25 | 26 | 27 |
| BV/h | 1.3 | 2.3 | 2.3 | 2.4 | 2.3 | recycle | recycle | recycle | recycle | 1.3 | 0.8 | 0.9 |
| DP1 | 49.1 | 48.9 | 49.1 | 48.9 | 48.6 | 59.9 | 64.9 | 67.9 | 69.4 | 50.9 | 54.4 | 54.5 |
| DP2 | 24.3 | 24.4 | 24.3 | 24.4 | 24.4 | 24.8 | 24.4 | 23.6 | 22.7 | 24.4 | 24.5 | 24.5 |
| DP3 | 16.9 | 16.9 | 16.9 | 17.0 | 17.0 | 9.4 | 7.5 | 6.3 | 5.7 | 15.7 | 13.6 | 13.5 |
| DP4 | 5.2 | 5.3 | 5.2 | 5.3 | 5.3 | 2.8 | 1.8 | 1.4 | 1.2 | 4.7 | 4.1 | 4.0 |
| DP5 | 2.0 | 1.9 | 1.8 | 1.8 | 1.9 | 1.5 | 0.8 | 0.6 | 0.8 | 1.9 | 1.5 | 1.5 |
| DP6 | 0.5 | 0.5 | 0.5 | 0.5 | 0.6 | 0.4 | 0.2 | 0.1 | 0.3 | 0.5 | 0.4 | 0.4 |
| DP7 | 0.2 | 0.2 | 0.2 | 0.2 | 0.2 | 0.1 | 0.1 | 0.1 | 0.0 | 0.2 | 0.2 | 0.2 |
| DP8 | 0.1 | 0.1 | 0.1 | 0.1 | 0.1 | 0.1 | 0.0 | 0.0 | 0.0 | 0.1 | 0.1 | 0.1 |
| DP9 | 0.1 | 0.1 | 0.1 | 0.1 | 0.1 | 0.0 | 0.0 | 0.0 | 0.0 | 0.0 | 0.1 | 0.1 |
| DP10 | 0.0 | 0.0 | 0.0 | 0.0 | 0.1 | 0.0 | 0.0 | 0.0 | 0.0 | 0.0 | 0.0 | 0.0 |
| DP11+ | 1.6 | 1.7 | 1.7 | 1.7 | 1.7 | 0.9 | 0.3 | 0.0 | 0.0 | 1.6 | 1.0 | 1.2 |

Table 19 clearly shows that a decrease in flow rate leads to a further degradation of the DPn fraction. This is also exemplified in table 20.

TABLE 20

| DAYS | BV/h | DP1 | DP2 | DP3 | DP4 | DPn |
|---|---|---|---|---|---|---|
| imo substrate | | 27.3 | 26.2 | 22.3 | 10.5 | 13.7 |
| 1 | 8.3 | 41.8 | 24.8 | 19.7 | 7.5 | 6.2 |
| 2 | 8.7 | 40.8 | 25.1 | 19.9 | 7.7 | 6.5 |
| 3 | 9.5 | 39.8 | 25.3 | 20.1 | 8.1 | 6.7 |
| 4 | 9.6 | 39.1 | 25.4 | 20.3 | 8.2 | 7.0 |
| 5 | 11.2 | 39.2 | 25.4 | 20.2 | 8.2 | 7.0 |
| 6 | 11.8 | 38.7 | 25.5 | 20.3 | 8.3 | 7.2 |
| 7 | 13 | 37.7 | 25.5 | 20.5 | 8.5 | 7.8 |
| 8 | 14.2 | 36.6 | 26 | 20.6 | 8.9 | 7.9 |
| 9 | 15.2 | 36.5 | 25.9 | 20.7 | 8.9 | 8.0 |
| 10 | 15.6 | 35.8 | 26 | 20.6 | 9.3 | 8.3 |
| 11 | 16.4 | 35.6 | 26 | 20.6 | 9.3 | 8.5 |
| 12 | 1.3 | 49.1 | 24.3 | 16.9 | 5.4 | 4.3 |
| 13 | 2.3 | 48.9 | 24.4 | 16.9 | 5.5 | 4.3 |
| 14 | 2.3 | 49.1 | 24.3 | 16.9 | 5.5 | 4.2 |
| 15 | 2.4 | 48.9 | 24.4 | 17.0 | 5.5 | 4.2 |
| 18 | 2.3 | 48.6 | 24.4 | 17.0 | 5.6 | 4.4 |
| 19 | Recycle | 59.9 | 24.8 | 10.1 | 3.0 | 2.2 |
| 20 | Recycle | 64.9 | 24.4 | 7.5 | 1.9 | 1.3 |
| 21 | Recycle | 67.9 | 23.6 | 6.3 | 1.5 | 0.7 |

TABLE 20-continued

| DAYS | BV/h | DP1 | DP2 | DP3 | DP4 | DPn |
|---|---|---|---|---|---|---|
| 22 | Recycle | 69.4 | 22.7 | 5.7 | 1.4 | 0.8 |
| 25 | 1.3 | 50.9 | 24.4 | 15.7 | 5.1 | 3.9 |
| 26 | 0.8 | 54.4 | 24.5 | 13.6 | 4.3 | 3.2 |
| 27 | 0.9 | 54.5 | 24.5 | 13.5 | 4.3 | 3.2 |

By adjusting the flow rate, a maximum amount of DPn fraction can be degraded, without hydrolysing too much the isomalto-oligosaccharides (table 21).

TABLE 21

| Days | BV/h | Dex-trose | Iso-mal-tose | Nige-rose | Mal-tose | Pa-nose | Iso-pa-nose | Iso-malto-triose | Malto-triose | Glucosyl-malto-triose | Isomal-tote-traose | Malto-tetra-ose | Iso total | DPn |
|---|---|---|---|---|---|---|---|---|---|---|---|---|---|---|
| | substrate | 2.8 | 0.4 | 0.0 | 49.7 | 0.2 | 0.2 | 0.0 | 20.0 | 0.1 | 0.0 | 0.9 | 0.9 | 25.7 |
| | imo syrup | 27.3 | 18.4 | 1.8 | 5.9 | 9.1 | 0.4 | 10.6 | 2.1 | 5.7 | 1.7 | 3.2 | 47.8 | 13.7 |
| 1 | 8.3 | 41.8 | 19.6 | 2.0 | 3.2 | 8.7 | 0.1 | 10.4 | 0.5 | 2.7 | 3.1 | 1.3 | 46.6 | 6.7 |
| 2 | 8.7 | 40.8 | 19.5 | 2.0 | 3.5 | 8.9 | 0.1 | 10.4 | 0.5 | 2.9 | 3.2 | 1.3 | 47.0 | 6.9 |
| 3 | 9.5 | 39.8 | 19.5 | 2.0 | 3.8 | 9.1 | 0.1 | 10.4 | 0.5 | 3.1 | 3.2 | 1.3 | 47.4 | 7.2 |
| 5 | 11.2 | 39.2 | 19.4 | 2.0 | 4.1 | 9.2 | 0.1 | 10.2 | 0.7 | 2.7 | 2.8 | 1.1 | 46.4 | 8.5 |
| 6 | 11.8 | 38.7 | 19.4 | 2.0 | 4.1 | 9.0 | 0.1 | 10.5 | 0.7 | 4.0 | 2.1 | 1.6 | 47.1 | 7.8 |
| 7 | 13.0 | 37.7 | 19.1 | 1.9 | 4.5 | 9.0 | 0.1 | 10.8 | 0.7 | 3.3 | 3.5 | 1.2 | 47.6 | 8.3 |
| 8 | 14.2 | 36.6 | 19.0 | 2.0 | 5.0 | 9.0 | 0.1 | 10.9 | 0.6 | 1.0 | 5.3 | 1.9 | 47.3 | 8.6 |
| 9 | 15.2 | 36.5 | 19.0 | 2.0 | 4.9 | 9.1 | 0.1 | 11.0 | 0.6 | 1.0 | 5.5 | 1.8 | 47.6 | 8.6 |
| 10 | 15.6 | 35.8 | 19.0 | 1.9 | 5.1 | 9.0 | 0.1 | 10.7 | 0.8 | 3.7 | 3.5 | 1.3 | 48.0 | 9.1 |
| 11 | 16.4 | 35.6 | 18.8 | 2.0 | 5.3 | 9.2 | 0.1 | 10.4 | 0.9 | 1.2 | 5.2 | 2.2 | 46.9 | 9.2 |
| 13 | 2.3 | 48.9 | 20.4 | 2.1 | 1.9 | 6.5 | 0.1 | 9.9 | 0.4 | 1.1 | 3.3 | 1.0 | 43.4 | 4.5 |
| 14 | 2.3 | 49.1 | 20.4 | 2.0 | 1.8 | 6.5 | 0.0 | 10.0 | 0.4 | 1.0 | 3.3 | 0.9 | 43.3 | 4.5 |
| 15 | 2.4 | 48.9 | 20.7 | 2.0 | 1.8 | 6.7 | 0.0 | 9.9 | 0.4 | 1.1 | 3.3 | 1.0 | 43.5 | 4.4 |
| 18 | 2.3 | 48.6 | 20.5 | 2.1 | 1.9 | 6.5 | 0.2 | 10.0 | 0.4 | 1.1 | 3.3 | 0.9 | 43.5 | 4.7 |
| 25 | 1.3 | 50.9 | 20.4 | 2.3 | 1.7 | 5.5 | 0.1 | 9.1 | 1.0 | 0.9 | 3.8 | 0.0 | 42.1 | 4.3 |
| 26 | 0.8 | 54.4 | 20.6 | 2.4 | 1.6 | 3.9 | 0.1 | 8.5 | 1.0 | 0.6 | 3.5 | 0.0 | 39.6 | 3.4 |
| 27 | 0.9 | 54.5 | 20.6 | 2.4 | 1.6 | 3.9 | 0.0 | 8.5 | 1.1 | 0.6 | 3.4 | 0.0 | 39.3 | 3.5 |

EXAMPLE 10

Immobilised Pullulanase Followed by an Immobilised Transglucosidase

A) Preparation of Immobilised Pullulanase 5 ml of Duolite A568 was washed with demineralized water to remove fines. The resin was subsequently conditioned with 0.15 ml of 1M $Na_2CO_3$. 7.5 g of Optimax 300L (Genencor) was added, followed by the addition of 0.008 ml glutaric dialdehyde solution (25% w/v)/ml of supernatant. The mixture was gently stirred overnight at ambient temperature. The produced conjugate was rinsed with demineralized water and put into a double jacketed glass column at 50° C. A 30% ds maltose syrup, brought at pH 4.2 was pumped through the column at an initial flow rate of 6 BV/h (bed volumes/hour). The column temperature was kept at 50° C. The debranching activity of the conjugate is clearly shown in table 22. The debranched maltose syrup was sent through an immobilised transglucosidase conjugate, as described in B).

TABLE 22

| DAYS | | 1 | 2 | 6 | 9 | 16 | 20 | 22 | 27 | 29 |
|---|---|---|---|---|---|---|---|---|---|---|
| BV/h | substrate | 2.8 | 5.9 | 6.3 | 6.0 | 6.0 | 5.9 | 6.0 | 6.0 | 5.7 |
| DP1 | 3.1 | 3.5 | 3.4 | 3.1 | 2.9 | 3.0 | 3.2 | 3.0 | 2.9 | 3.0 |
| DP2 | 50.6 | 50.5 | 50.3 | 50.5 | 50.7 | 50.6 | 50.2 | 50.3 | 50.5 | 50.6 |
| DP3 | 19.8 | 22.6 | 22.6 | 22.8 | 22.7 | 22.7 | 22.3 | 22.3 | 22.4 | 22.2 |
| DP4 | 0.7 | 3.8 | 3.7 | 3.9 | 3.9 | 3.6 | 3.6 | 3.7 | 3.6 | 3.5 |
| DP5 | 1.0 | 4.9 | 4.8 | 5.0 | 5.0 | 5.0 | 5.1 | 5.2 | 5.0 | 5.1 |
| DP6 | 1.5 | 2.8 | 2.8 | 2.8 | 2.8 | 2.8 | 2.9 | 3.0 | 3.0 | 2.9 |
| DP7 | 2.9 | 2.4 | 2.4 | 2.3 | 2.3 | 2.5 | 2.5 | 2.4 | 2.5 | 2.5 |
| DP8 | 3.4 | 1.3 | 1.4 | 1.4 | 1.4 | 1.4 | 1.5 | 1.5 | 1.4 | 1.4 |
| DP9 | 2.0 | 1.0 | 1.0 | 1.0 | 1.0 | 1.0 | 1.0 | 1.1 | 1.0 | 1.0 |
| DP10 | 0.7 | 0.6 | 0.7 | 0.7 | 0.6 | 0.6 | 0.6 | 0.6 | 0.6 | 0.6 |
| DP11+ | 14.3 | 6.5 | 6.8 | 6.5 | 6.7 | 6.8 | 7.0 | 7.0 | 7.0 | 7.1 |

B) Preparation of Immobilised Transglucosidase 5 ml of Duolite A568 was washed with demineralized water to remove fines. The resin was subsequently conditioned with 0.15 ml of 1M $Na_2CO_3$. 1 g of Transglucosidase L "Amano" was added, followed by the addition of 0.08 ml glutaric dialdehyde solution (25% w/v). The mixture was gently stirred overnight at ambient temperature. The produced conjugate was rinsed with demineralized water and put into a double jacketed glass column at 50° C. The syrupproduced by the pullulanase conjugate was pumped through the column at an initial flow rate of 6 BV/h (bed volumes/hour). The column temperature was kept at 50° C. The production of isomalto-oligosaccharide syrup is shown in table 23.

TABLE 23

| DAYS | BV/h | Iso total | DPn |
|---|---|---|---|
| | HMS | 0.5 | 25.8 |
| 2 | 5.9 | 47.4 | 18.1 |
| 6 | 6.3 | 45.9 | 19.3 |
| 8 | 6.4 | 47.2 | 16.7 |
| 9 | 6.0 | 45.0 | 17.7 |
| 13 | 6.0 | 46.7 | 19.1 |
| 16 | 6.0 | 48.1 | 18.0 |
| 20 | 5.9 | 46.6 | 18.7 |
| 22 | 6.0 | 47.0 | 18.6 |
| 27 | 6.0 | 44.5 | 18.6 |
| 29 | 5.7 | 46.0 | 18.7 |

EXAMPLE 11

Regeneration of the Resin and Reloading with Enzyme

A) 10 ml of Duolite A568™ was washed with demineralized water to remove fines. The resin was subsequently conditioned with 0.3 ml of 1M $Na_2CO_3$. 1 g of Transglucosidase L "Amano" (liquid preparation, 11.2 mg protein/g enzyme solution, 103 TGU/g enzyme solution) were added, and the mixture was stirred for 4 h at room temperature. Subsequently 15 g of pullulanase (Optimax L300™ from Genencor Int., 2.6 mg protein/g enzyme solution, 400 PU/g enzyme solution) was added, and the immobilisation was continued for another 4 h. 5 ml of a 1.0% glutaric dialdehyde solution was added to give a 0.2% glutaric dialdehyde solution, and the resin was stirred for one night at ambient temperature. The produced conjugate was rinsed with demineralized water and put into a double jacketed glass column at 50° C. A 30% ds maltose syrup, brought to pH 4.2 was pumped through the column at a flow rate of 10 BV/h (bed volumes/hour). The column temperature was kept at 50° C.

The conjugate was run for 30 days producing 43–45% isomalto-oligosaccharides at 3 BV/h.

B) Subsequently the conjugate was transported to a beaker and washed with water to el iminate sugars and fines. The pH of the resin was brought to 1.5 and the resin was stirred for 1 h at 60° C. The pH was then raised to 12.5 with NaOH, and stirring was continued for 1 h while maintaining the pH at 12.5. Thereafter the conjugate was washed with demineralised water to eliminate fines.

C) Procedure A) was repeated on the regenerated resin. A same amount of enzyme was immobilised and the new conjugate produced a 43–45% isomalto-oligosaccharide syrup at the same flow rate as described in A

We claim:

1. A method for producing an isomalto-oligosaccharide containing syrup wherein a starch hydrolysate is enzymatically converted by a transglucosidase immobilized on a re-usable carrier.

2. A method according to claim 1, wherein the starch hydrolysate has a DE of between 4 and 70.

3. A method according to claim 1, wherein the carrier is an anion exchange resin and the transglucosidase is immobilized onto it by adsorption.

4. A method according to claim 1, wherein other enzymes are co-immobilized with the transglucosidase, wherein said other enzymes are selected from the group consisting of pullulanases and alpha-amylases, and wherein the co-immobilisation is performed using one or more separate carriers.

5. A method according to claim 1, wherein the carrier/enzyme conjugate is further reinforced by reaction with a cross-linking agent.

6. A method according to claim 5, wherein the cross-linking agent is glutaric dialdehyde.

7. A method according to claim 1, wherein the isomalto-oligosaccharide contains more than 40% isomalto-oligosaccharides, and that these values are achieved with a flow rate of at least 3 bed volumes per hour and for a period of at least 25 days.

8. A method according to any one of claims 1–7 wherein the isomalto-oligosaccharide syrup is further refined.

9. A method according to claim 1, wherein during the production of the isomalto-oligosaccharide syrup or thereafter the sweetness is increased by the addition of a sweetener or by an additional enzymatic conversion with glucose isomerase or a hydrolase.

10. A method according to claim 2, wherein the starch hydrolysate has a DE of between 20 and 60.

11. A method according to claim 7, wherein the isomalto-oligosaccharide contains more than 45% isomalto-oligosaccharides, and that these values are achieved with a flow rate of at least 3 bed volumes per hour and for a period of at least 25 days.

12. A method according to claim 8, wherein the isomalto-oligosaccharide syrup is refined by chromatographic means or filtration.

13. A method according to claim 1, wherein the method further comprises recovering said re-usable carrier.

14. A method according to claim 13, wherein said recovered re-usable carrier is loaded with an enzyme.

15. A method for producing an isomalto-oligosaccharide containing syrup comprising:

conducting an enzymatical converting a starch hydrolysate having a DE between 4 and 70 using a transglucosidase immobilized on a re-usable carrier and other enzymes co-immobilized on said re-usable carrier or co-immobilized on one or more separate reusable carriers, said other enzymes being selected from the group consisting pullulanases and alpha-amylases; and refining further the thus obtained isomalto-oligosaccharide syrup.

16. A method according to claim 15, wherein said other enzymes are co-immobilized on at least one other re-usable carriers, and wherein said method starch hydrolysate is enzymatically converted using said other co-immobilized enzymes, and then treated with said immobilized transglucosidase.

17. A method according to claim 15, wherein said co-immobilized enzymes are stabilized.

18. A method according to claim 15, wherein the method further comprises:

conducting said enzymatic conversion until the enzymatic activity decreases to a pre-determined value;

recovering at least one said re-usable carrier, and freeing the recovered re-usable carrier of enzyme; and re-loading the recovered carrier with a selected enzyme.

19. A method according to claim 15, wherein said re-usable carrier comprises an anion exchange resin.

* * * * *